United States Patent
Okamura et al.

(10) Patent No.: US 10,124,150 B2
(45) Date of Patent: *Nov. 13, 2018

(54) INTRODUCER

(71) Applicant: TERUMO KABUSHIKI KAISHA, Shibuya-ku (JP)

(72) Inventors: Ryo Okamura, Fujinomiya (JP); Yushin Yazaki, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1015 days.

This patent is subject to a terminal disclaimer.

(21) Appl. No.: 14/496,425

(22) Filed: Sep. 25, 2014

(65) Prior Publication Data

US 2015/0133865 A1    May 14, 2015

Related U.S. Application Data

(63) Continuation of application No. PCT/JP2013/058121, filed on Mar. 21, 2013.

(30) Foreign Application Priority Data

Mar. 27, 2012  (JP) ................ 2012-072408

(51) Int. Cl.
| | |
|---|---|
| *A61M 25/06* | (2006.01) |
| *A61M 29/00* | (2006.01) |
| *A61M 39/06* | (2006.01) |
| *A61M 25/00* | (2006.01) |

(52) U.S. Cl.
CPC ........ *A61M 25/0662* (2013.01); *A61M 29/00* (2013.01); *A61M 39/06* (2013.01);
(Continued)

(58) Field of Classification Search
CPC .. A61M 25/0662; A61M 39/06; A61M 29/00; A61M 2025/0008;
(Continued)

(56) References Cited

U.S. PATENT DOCUMENTS

| | | | | | |
|---|---|---|---|---|---|
| 5,139,486 A | * | 8/1992 | Moss | ................ | A61M 25/0662 604/158 |
| 5,741,233 A | * | 4/1998 | Riddle | .............. | A61M 25/0097 604/160 |

(Continued)

FOREIGN PATENT DOCUMENTS

| | | |
|---|---|---|
| JP | 6-48684 U | 7/1994 |
| JP | 2007-523680 A | 8/2007 |

(Continued)

OTHER PUBLICATIONS

"Merit Medical Recalls Prelude Short Sheath Catehter Introducer", Diagnostic and Intervential Cardiology, News, dated Feb. 8, 2011, available online Mar. 15, 2018 at https://www.dicardiology.com/content/merit-medical-recalls-prelude-short-sheath-catheter-introducer.*

(Continued)

*Primary Examiner* — Amber Stiles
(74) *Attorney, Agent, or Firm* — Buchanan Ingersoll & Rooney PC

(57) ABSTRACT

An introducer is configured to distinguish an introducer provided with a sheath tube whose wall thickness is reduced, from an introducer provided with a sheath tube whose wall thickness is not reduced, and to recognize the relationship between the inner diameter and the outer diameter for the sheath tube in which the wall thickness is reduced. An introducer includes an introducer sheath and a dilator. The introducer further includes a first information piece on at least one of the introducer sheath and the dilator and has an inner diameter dimension of the sheath tube as an index.

(Continued)

Furthermore, a second information piece having an outer diameter dimension of the sheath tube as an index is on at least one of the introducer sheath and the dilator.

19 Claims, 7 Drawing Sheets

(52) U.S. Cl.
CPC . *A61M 39/0606* (2013.01); *A61M 2025/0008* (2013.01); *A61M 2025/0681* (2013.01); *A61M 2039/062* (2013.01); *A61M 2039/064* (2013.01); *A61M 2039/066* (2013.01); *A61M 2039/0653* (2013.01); *A61M 2205/60* (2013.01); *A61M 2205/6081* (2013.01)

(58) Field of Classification Search
CPC .. A61M 2025/0681; A61M 2205/6081; A61M 2205/60; A61M 39/0606; A61M 2039/0653; A61M 2039/064; A61M 2039/066; A61M 2039/062
See application file for complete search history.

(56) References Cited

U.S. PATENT DOCUMENTS

| | | | |
|---|---|---|---|
| 2003/0047126 A1* | 3/2003 | Tomaschko | A61B 50/30 |
| | | | 116/201 |
| 2014/0114290 A1 | 4/2014 | Okamura | |
| 2015/0032056 A1* | 1/2015 | Okamura | A61M 25/0662 |
| | | | 604/164.1 |

FOREIGN PATENT DOCUMENTS

| | | |
|---|---|---|
| WO | WO 97/14468 A1 | 4/1997 |
| WO | WO 2005/007024 A2 | 1/2005 |
| WO | WO 2009/131833 A2 | 10/2009 |
| WO | WO 2013/002286 A1 | 1/2013 |

OTHER PUBLICATIONS

International Search Report (PCT/ISA/210) dated May 21, 2013, by the Japanese Patent Office as the International Searching Authority for International Application No. PCT/JP2013/058121.

* cited by examiner

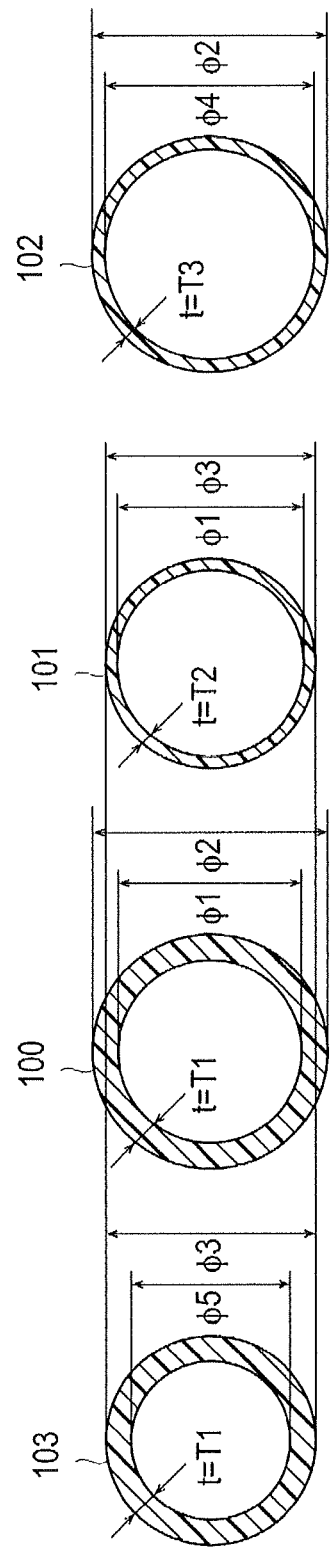

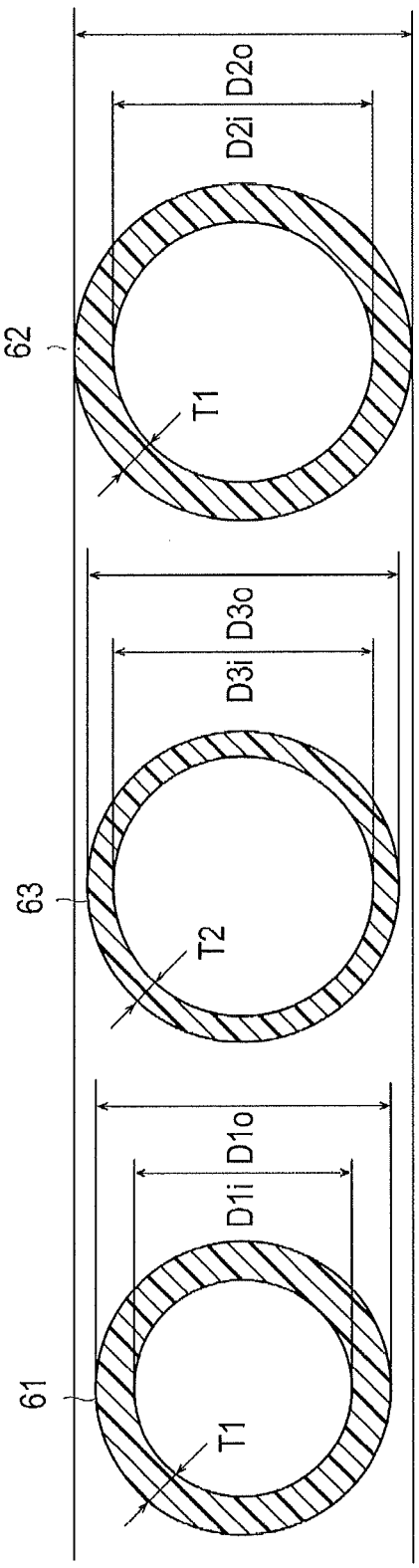

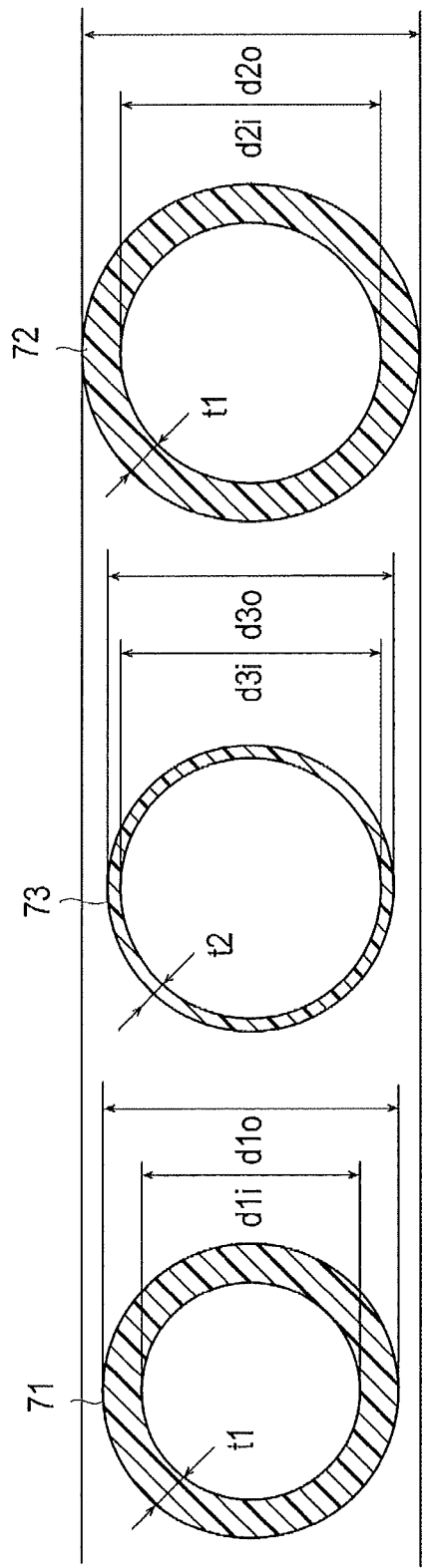

INTRODUCER

CROSS-REFERENCES TO RELATED APPLICATIONS

This application is a continuation of International Application No. PCT/JP2013/058121 filed on Mar. 21, 2012, and claims priority to Japanese Application No. 2012-072408 filed on Mar. 27, 2012, the entire content of both of which is incorporated herein by reference.

TECHNICAL FIELD

The present invention generally relates to an introducer.

BACKGROUND DISCUSSION

In recent years, various types of treatments and diagnoses in the medical field have been performed using an elongated and hollow tubular-shaped medical instrument called a catheter. Examples of such treatment methods include directly administering an agent into an affected area using the elongated configuration of the catheter, push-opening a narrowed section in the lumen in a living body using a catheter in which a balloon expanded by pressure is attached to a distal end of the catheter, scraping and opening the affected area using a catheter in which a cutter is attached to a distal portion of the catheter, and closing arterial aneurysm, bleeding, or feeding blood vessel sites with a filling material using the catheter. Other examples also include a treatment method of embedding and placing a tubular-shaped stent which has a mesh-shaped side surface into the lumen in the living body using the catheter so as to maintain an open state of the narrow section in the lumen in the living body. Further, examples include aspirating a thrombus within the blood vessels.

In general, an introducer is used in a case where the treatment, diagnosis, or the like is performed using the catheter. The introducer has an introducer sheath including a sheath tube introduced to a puncture site; a dilator which is inserted into a lumen of the sheath tube; and a three-way stopcock portion which is provided so as to be communicated with the lumen of the sheath tube. An example is disclosed in Japanese Utility Model No. 6-48684. The sheath tube is introduced to a puncture site which is formed on an arm or a leg and a catheter or the like is percutaneously inserted into a lesion site such as the blood vessel through the lumen of the sheath tube.

In general, the introducer is color-coded based on a color code. The color code shows a maximum diameter of a device (medical instrument such as a catheter) that can be inserted into the lumen of the sheath tube in the introducer sheath using colors.

SUMMARY

Consideration has been given to reducing the wall thickness of a sheath tube to more easily introduce the sheath tube to a puncture site by making the outer diameter of the sheath tube small and to make a device with a large outer diameter to be able to be inserted by making the inner diameter of the sheath tube large.

Regarding an introducer provided with the sheath tube of which the wall thickness is reduced, in a case where a color code which is the same as that of a previous sheath tube is used, there is a problem in that it is impossible to easily recognize the difference with an introducer provided with the previous sheath tube in which the wall thickness is not reduced.

Such a problem also arises even in both cases before and after setting the introducer sheath and the dilator.

In addition, with respect to the sheath tube in which the wall thickness is reduced, there is a problem in that it is impossible to recognize the relationship between the inner diameter and the outer diameter. For this reason, it is impossible to recognize whether or not the introducer is an introducer provided with a sheath tube in which the outer diameter is reduced while maintaining the maximum diameter of the insertable medical instrument as it is in the previous sheath tube, or an introducer provided with a sheath tube in which the maximum diameter of the insertable medical instrument is made large while maintaining the outer diameter dimension as it is in the previous sheath tube.

The introducer disclosed here makes it possible to rather easily distinguish the introducer provided with the sheath tube in which the wall thickness is reduced, from the introducer provided with the previous sheath tube in which the wall thickness is not reduced, and makes it possible to relatively easily recognize the relationship between the inner diameter and the outer diameter regarding the sheath tube in which the wall thickness is reduced.

An introducer includes an introducer sheath having an elongated hollow sheath tube and a sheath hub which is provided at a proximal side of the sheath tube and provided with an insertion port through which a dilator is inserted; a dilator having a dilator tube which is inserted into the sheath tube and a dilator hub which is provided at a proximal side of the dilator tube; and a first information piece which is shown on at least one of the introducer sheath and the dilator and has an inner diameter dimension of the sheath tube as an index, and a second information piece which is shown on at least one of the dilator and the introducer sheath and has an outer diameter dimension of the sheath tube as an index.

The first information piece or the second information piece shown on the dilator is shown on at least one of the dilator tube and the dilator hub, and the first information piece or the second information piece shown on the introducer sheath is shown on at least one of the sheath tube and the sheath hub.

The first information piece is shown at a position closer to the proximal portion of the dilator than the second information piece.

The sheath hub includes a sheath support body which is provided at a proximal side of the sheath tube; a housing which is provided at a proximal side of the sheath support body; a cap which is attached to the housing and at which the insertion port is formed; and a tab portion in which a through hole is formed in order to positionally fix the introducer sheath. The first information piece is shown on at least one of the sheath support body, the housing, the cap, and the tab portion in the sheath hub, and the second information piece is shown on at least one of the sheath support body, the housing, the cap, and the tab portion in the sheath hub.

The sheath tube to be applied includes (a) a first sheath tube in which the wall thickness is T1 and the outer diameter dimension is D1o, (b) a second sheath tube in which the wall thickness is T1 which is the same as the wall thickness of the first sheath tube and the outer diameter dimension is D2o (D1o<D2o) which is a size larger than the first sheath tube, and (c) a third sheath tube in which the wall thickness is T2(T2<T1) which is thinner than the wall thicknesses of the first and the second sheath tubes, the outer diameter dimension is D3o(D1o<D3o<D2o) which is larger than the outer diameter dimension D1o of the first sheath tube and smaller than the outer diameter dimension D2o of the second sheath tube, and the inner diameter dimension is D3i (D1i<D3i≤D2i) which is larger than the inner diameter dimension D1i of the first sheath tube and not larger than the inner diameter dimension D2i of the second sheath tube. The first information piece shown when applied to the third sheath tube is the same as the first information piece shown when applied to the second sheath tube, and the second information piece shown when applied to the third sheath tube is the same as the second information piece shown when applied to the first sheath tube.

The sheath tube to be applied includes (a) a first sheath tube in which the wall thickness is T1 and the outer diameter dimension is d1o, (b) a second sheath tube in which the wall thickness is t1 which is the same as the wall thickness of the first sheath tube and the outer diameter dimension is d2o (d1o<d2o) which is a size larger than the outer diameter dimension of the first sheath tube, and (c) a third sheath tube in which the wall thickness is t2(t2<t1) which is thinner than the wall thicknesses of the first and the second sheath tubes, the outer diameter dimension is d3o(d3o<d1o<d2o) which is smaller than the outer diameter dimension d1oof the first sheath tube, and the inner diameter dimension is d3i (d1i<d3i≤d2i) which is larger than the inner diameter dimension d1i of the first sheath tube and not larger than the inner diameter dimension d2i of the second sheath tube.

The first information piece shown when applied to the third sheath tube is the same as the first information piece shown when applied to the second sheath tube, and The second information piece shown when applied to the third sheath tube is the same as the second information piece shown when applied to the first sheath tube.

The first information piece is at least one of a color or a figure, and the second information piece is at least one of a color or a figure.

The introducer disclosed here includes the first information piece having the inner diameter dimension of the sheath tube as an index and the second information piece having the outer diameter dimension of the sheath tube as an index, on the introducer sheath or the dilator. Therefore, it is possible to easily recognize the difference between the introducer provided with the sheath tube in which the wall thickness is reduced and the introducer provided with the previous sheath tube in which the wall thickness is not reduced. For example, in a case where the first information piece is a Fr size of the sheath tube having an inner diameter dimension of the sheath tube as an index and the second information piece is a Fr size of the sheath tube having an outer diameter dimension of the sheath tube as an index, the first information piece and the second information piece are the same as each other in a case of the previous sheath tube in which the wall thickness is not reduced.

On the other hand, in a case of the sheath tube in which the wall thickness is reduced, it is possible to reduce the size of the outer diameter dimension by, for example, reducing one Fr size at the same inner diameter dimension, and therefore, the first information piece and the second information piece are different from each other. In other words, when the first information piece and the second information piece are the same as each other, a user can easily identify that the used introducer is the introducer provided with the previous sheath tube in which the wall thickness is not reduced. Meanwhile, when the first information piece and the second information piece are different from each other, a user can easily identify that the used introducer is the introducer provided with the sheath tube in which the wall thickness is reduced.

Furthermore, since the introducer is provided with the first information piece having the inner diameter dimension of the sheath tube as an index and the second information piece having the outer diameter dimension of the sheath tube as an index, the relationship between the inner diameter and the outer diameter becomes clear with respect to the sheath tube in which the wall thickness is reduced.

In this manner, a user can recognize whether or not the sheath tube is the sheath tube in which the wall thickness is reduced and can recognize the relationship between the inner diameter and the outer diameter with respect to the sheath tube in which the wall thickness is reduced while preparing or using the introducer. Accordingly, it is possible to smoothly and promptly proceed with the preparation work of a device to be inserted next and to prevent misidentification of the device size.

It is possible to employ a mode showing both the first information piece and the second information piece on the introducer. Moreover, individual members which are included in the introducer sheath can be set to show the first information piece or the second information piece and individual members which are included in the dilator can be set to show the first information piece or the second information piece.

When a user inserts the dilator tube into the sheath tube, the user grips and presses the dilator hub closer to the proximal portion of the dilator. The inner diameter of the sheath tube is thus shown at a position closer to the proximal portion of the dilator. Therefore, it is easy to recognize the maximum size of a device that can be inserted into the insertion port.

The effect described above can be exhibited by showing the first information piece on individual members of the sheath hub and the second information piece on individual members of the sheath hub.

The third sheath tube is the sheath tube in which the wall thickness is reduced compared to the wall thickness of the first and the second sheath tubes. The outer diameter dimension of the third sheath tube is the same as the outer diameter dimension of the first sheath tube and the inner diameter dimension is the same as the inner diameter dimension of the second sheath tube. Therefore, it is possible to insert a device having a size larger while reducing the size of the outer diameter.

The third sheath tube is the sheath tube in which the wall thickness is reduced compared to the wall thicknesses of the first and the second sheath tubes, and the outer diameter dimension of the third sheath tube is smaller than the outer diameter dimension of the first and the second sheath tubes. Therefore, it is possible to insert a device by reducing the size of the outer diameter. In addition, when the inner diameter dimension is a size between the inner diameter dimensions of the first and the second sheath tubes, a device having a size larger can be inserted.

It is also possible to simply show the first and the second information pieces using a color or a figure.

BRIEF DESCRIPTION OF DRAWINGS

FIGS. 5(A) and 5(D) are cross-sectional views showing sheath tubes in which the wall thicknesses (t=T1) are relatively thick and FIGS. 5(B) and 5(C) are cross-sectional views showing sheath tubes in which the wall thicknesses (t=T2, T3) are relatively thin.

FIGS. 6(A) to 6(C) are cross-sectional views illustrating first to third sheath tubes applied to an introducer. The third sheath tube is a sheath tube in which the wall thickness is more reduced compared to the first and the second sheath tubes. The third sheath tube shows a tube in which the outer diameter dimension is the same as that of the first sheath tube and the inner diameter dimension is the same as that of the second sheath tube and through which a device having a size larger can be inserted while reducing the size of the outer diameter.

FIGS. 7(A) to 7(C) are cross-sectional views illustrating first to third sheath tubes applied to an introducer. The third sheath tube is a sheath tube of which the wall thickness is more reduced compared to the first and the second sheath tubes. The third sheath tube shows a tube in which the outer diameter dimension is smaller than those of the first and second sheath tubes and through which a device can be inserted while reducing the size of the outer diameter.

DETAILED DESCRIPTION

Figure 1:
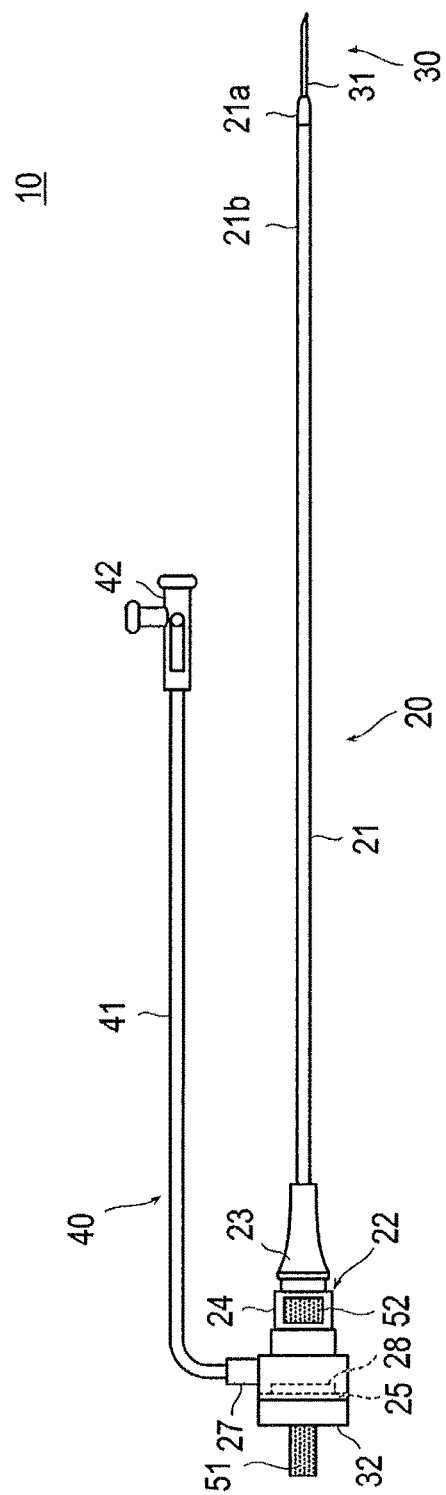
FIG. 1 is a plan view showing a schematic configuration of an introducer in a state where an introducer sheath and a dilator are set.

Hereinafter, an embodiment of an introducer representing one example of the introducer disclosed here will be described with reference to the accompanying drawings.

Common features are identified by the same reference numerals throughout and a detailed description of previously described features will not be repeated. In some cases, dimensional ratios in the drawings are exaggerated and are different from the actual ratios for the convenience of description.

Figure 2:
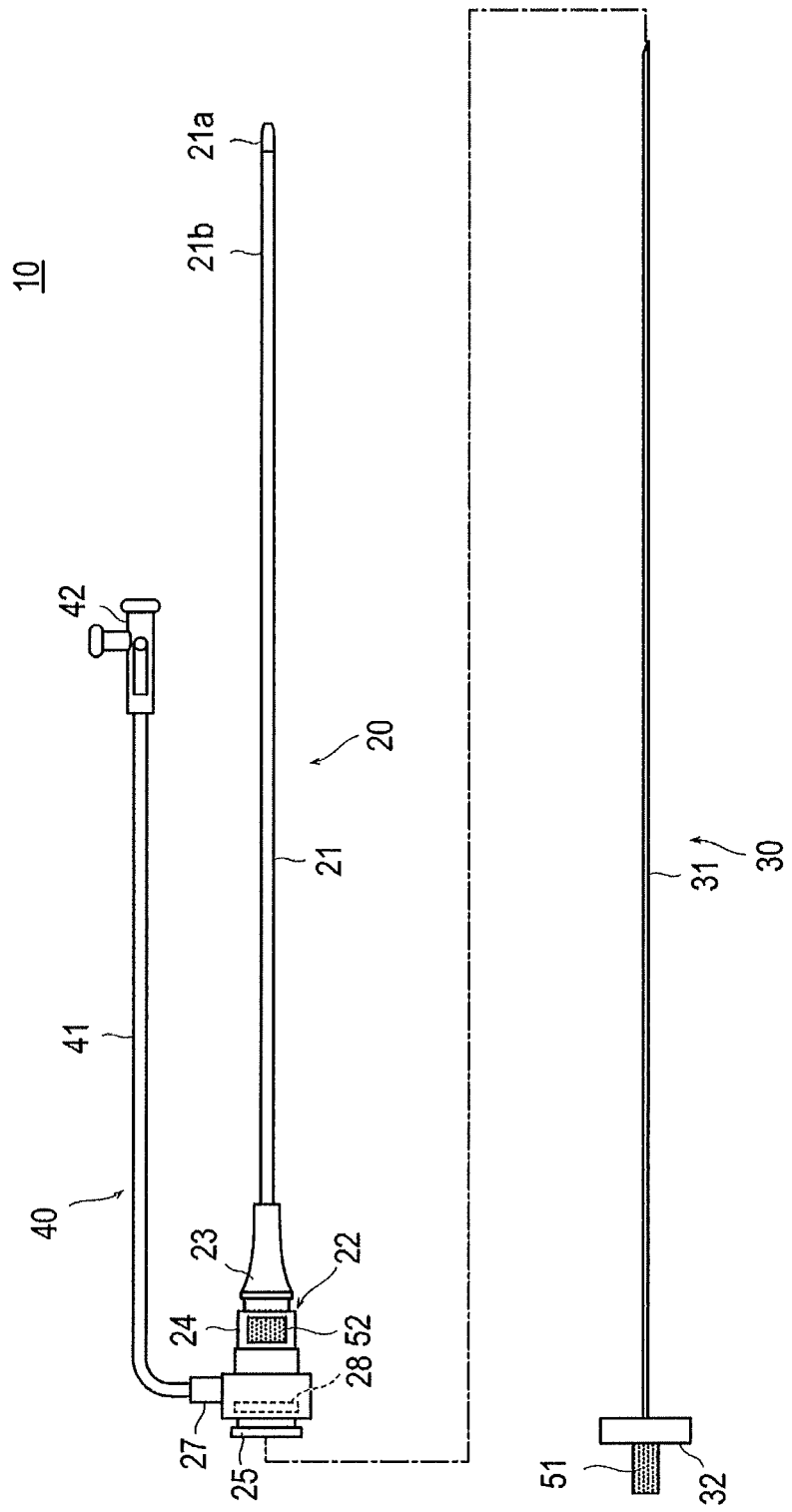
FIG. 2 is a plan view showing a schematic configuration of an introducer in a state where an introducer sheath and a dilator are disassembled.
Figure 3:
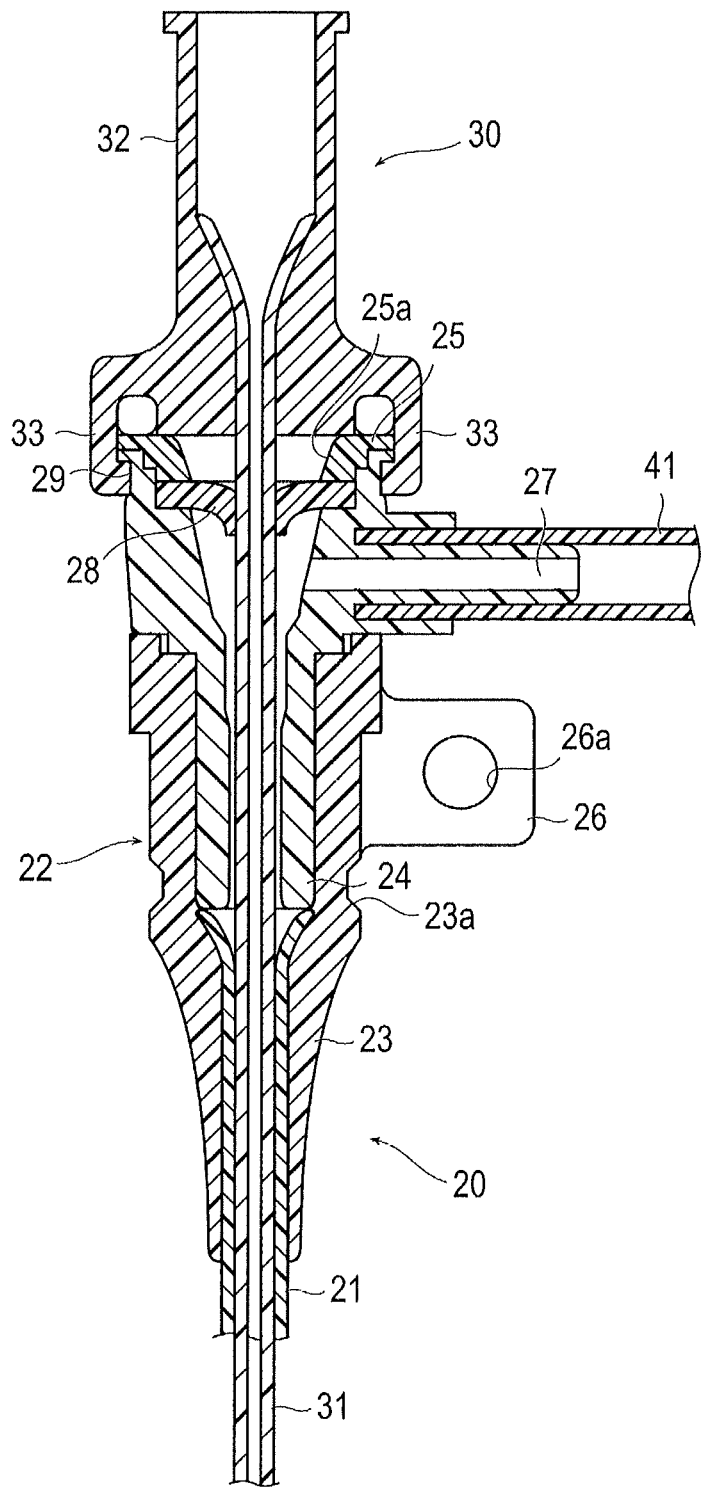
FIG. 3 is a cross-sectional view showing a main section of an introducer.
Figure 4:
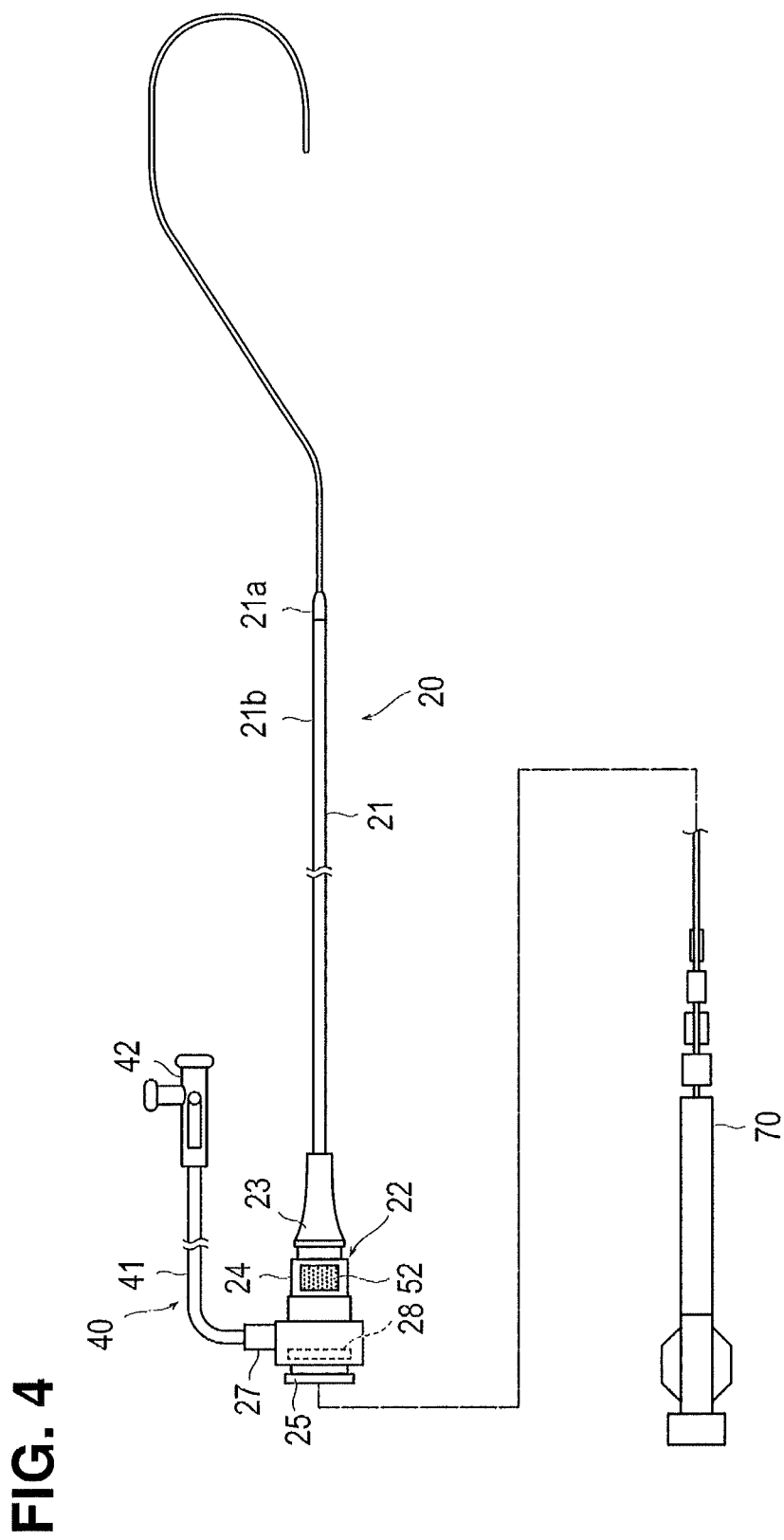
FIG. 4 is a view showing a state where a catheter is inserted through an introducer sheath introduced to a puncture site.

FIG. 1 illustrates the configuration of an introducer 10 in a state where an introducer sheath 20 and a dilator 30 are set, FIG. 2 shows the introducer 10 in a state where the introducer sheath 20 and the dilator 30 are disassembled, FIG. 3 is a cross-sectional view showing a main section of the introducer 10, and FIG. 4 illustrates a catheter 70 inserted through the introducer sheath 20 introduced to a puncture site.

The introducer 10 is a device that ensures an access route into a lumen in a living body. In the description below, the hand operation unit side of the device from which the device is operated will be referred to as a "proximal side" or "proximal end" and the side through which the device is inserted into the lumen in the living body will be referred to as a "distal side" or "distal end".

To outline the introducer 10 with reference to FIGS. 1 to 3, the introducer 10 includes the introducer sheath 20, the dilator 30, and a three-way stopcock portion 40. The introducer sheath 20 includes an elongated hollow sheath tube 21 and a sheath hub 22 which is provided at the proximal side of the sheath tube 21 and provided with an insertion port 25a through which the dilator 30 is inserted. The dilator 30 includes a dilator tube 31 which is inserted into (positioned in) the sheath tube 21 and a dilator hub 32 which is provided at the proximal side of the dilator tube 31 and is connectable to a sheath hub 22. The three-way stopcock portion 40 includes a connection tube 41 possessing one end connected to the sheath hub 22 and a three-way stopcock main body 42 which is connected to the other end of the connection tube 41. Referring to FIG. 4, the dilator 30 is removed after the introducer sheath 20 is introduced to a puncture site, and a device such as the catheter 70 is percutaneously inserted into a lesion site such as the blood vessels or the like through a lumen of the introducer sheath 20. Compared to trans femoral intervention (TFI) in which the introducer sheath 20 is introduced from a foot, trans radial intervention (TRI) in which the introducer sheath 20 is introduced from the arm has advantages such as facilitated hemostasis, shortened rest time, fewer bleeding complications, and the like for both patients and hospitals. Hereinafter, the introducer 10 will be described in detail.

The introducer sheath 20 remains in the lumen in the living body. A device such as the catheter 70, a guide wire, or an embolus material is inserted into the introducer sheath to be introduced into the lumen in the living body.

The sheath tube 21 is percutaneously introduced into the lumen in the living body. The sheath tube 21 possesses an elongated tubular shape and the proximal side of the sheath tube 21 is connected to the distal side of the sheath hub 22. The sheath tube 21 includes a distal portion 21a with a tapering outer diameter and a main body portion 21b with a constant outer diameter.

Examples of the material constituting the sheath tube 21 is not particularly limited, but it is possible to use a polymer material such as polyolefin (for example, polyethylene, polypropylene, polybutene, an ethylene-propylene copolymer, an ethylene-vinyl acetate copolymer, an ionomer, and a mixture of at least two thereof), a polyolefin elastomer, a cross-linked body of polyolefin, polyvinyl chloride, polyamide, a polyamide elastomer, polyester, a polyester elastomer, polyurethane, a polyurethane elastomer, fluorine resin, polycarbonate, polystyrene, polyacetal, polyimide, polyetherimide, and aromatic polyether ketone, and a mixture thereof. An ethylene tetrafluoroethylene copolymer (ETFE) can be used suitably.

As shown in FIG. 3, the sheath hub 22 includes a sheath support body 23 which is provided at the proximal side of the sheath tube 21; a housing 24 which is provided at the proximal side of the sheath support body 23; a cap 25 which is attached to the housing 24 and at which the insertion port 25a is formed; and a tab portion 26 in which a through hole 26a is formed in order to positionally fix the introducer sheath 20.

The diameter of the distal portion of the sheath support body 23 is reduced to have a curved-surface shape in order to prevent kinking of the sheath tube 21. It is preferable that the quality of the material of the sheath support body 23 be flexible resin in order to prevent the kinking of the sheath tube 21, and a thermoplastic elastomer such as SEBS can be used.

The distal side of the housing 24 is connected to the proximal side of the sheath support body 23 and the proximal side of the housing 24 extends over the sheath support body 23. A side port 27 that communicates with the lumen of the sheath tube 21 is formed on the side of the housing 24.

The material constituting the housing 24 is not particularly limited, but a hard material such as hard resin is suitable. Examples of the hard resins include polyolefin such as polyethylene and polypropylene, polyamide, polycarbonate, and polystyrene.

A hemostasis valve 28 is attached to the proximal side of the housing 24. The hemostasis valve 28 has a substantially elliptical membrane shape (disk-shape). The material constituting the hemostasis valve 28 is not particularly limited, but examples of the material include silicone rubber, latex rubber, butyl rubber, and isoprene rubber which are elastic members.

The cap 25 fixes the hemostasis valve 28 such that an outer peripheral part of the hemostasis valve 28 is interposed between the housing 24 and the cap 25 as shown in FIG. 3. The material constituting the cap 25 is not particularly limited, but the material which is the same as that constituting the housing 24 can be applied.

The tab portion 26 is integrally provided at the proximal side of the sheath support body 23 in the embodiment shown in the drawing. That is, in this embodiment representing an example of the introducer, the tab portion 26 and the sheath support body 23 are integrally formed in one piece as a unit. The hole 26a formed in the tab portion 26 and a fixing groove 23a formed on the sheath support body 23 are appropriately used to fix the introducer sheath 20 to the puncture site.

The tab portion 26 may be a separated body from the sheath support body 23. Furthermore, the tab portion 26 may be rotatably provided around the axis of the sheath tube 21 in order to easily adjust the position of the tab portion 26 during fixing work.

The dilator 30 is used to prevent the sheath tube 21 from being kinked and to expand the diameter of a perforation on the skin when the introducer sheath 20 is inserted into the blood vessel.

The dilator tube 31 is inserted into the sheath tube 21. As shown in FIG. 1, the dilator tube is configured so that the distal portion of the dilator tube 31 is able to protrude from (distally beyond) the distal end of the sheath tube 21.

Examples of materials constituting the dilator tube 31 include a polymer material such as polyolefin (for example, polyethylene, polypropylene, polybutene, an ethylene-propylene copolymer, an ethylene-vinyl acetate copolymer, an ionomer, and a mixture of at least two thereof), a polyolefin elastomer, a cross-linked body of polyolefin, polyvinyl chloride, polyamide, a polyamide elastomer, polyester, a polyester elastomer, polyurethane, a polyurethane elastomer, fluorine resin, polycarbonate, polystyrene, polyacetal, polyimide, polyetherimide, and aromatic polyether ketone, and a mixture thereof.

The dilator hub 32 includes a locking claw 33 that extends toward the distal side. The locking claw (distal part of the locking claw) 33 includes a projection that fits into an annular groove 29 which is provided at the proximal side of the sheath hub 22. The dilator hub 32 is detachably held at the sheath hub 22 using the locking claw 33 of the dilator hub 32 and the annular groove 29 of the sheath hub 22.

The material constituting the dilator hub 32 is not particularly limited, but a hard material such as hard resin is suitable. Examples of the hard resin include polyolefin such as polyethylene and polypropylene, polyamide, polycarbonate, and polystyrene.

An end of the connection tube 41 of the three-way stopcock portion 40 is liquid tightly connected to the side port 27 which is provided in the sheath hub 22. The connection tube 41 is a tube made of polybutadiene and has flexibility, for example. The three-way stopcock main body 42 is mounted on the other end of the connection tube 41. A liquid such as physiological saline is injected into the introducer sheath 20 through the connection tube 41 from a port of the three-way stopcock main body 42.

FIGS. 5(A) and 5(D) are cross-sectional views showing sheath tubes 100 and 103 possessing wall thicknesses (t=T1) that are relatively thick, and FIGS. 5(B) and 5(C) are cross-sectional views showing sheath tubes 101 and 102 possessing wall thicknesses (t=T2, T3) that are relatively thin.

As shown in FIGS. 5(A) and 5(B), the size of the outer diameter dimension $\phi 3$ can be reduced by, for example, one French size (Fr size) ($\phi 2 > \phi 3$) at the same inner diameter dimension $\phi 1$ by reducing the wall thickness (t=T2, T1>T2) of the sheath tube 101. Here, the French size (Fr size) of the sheath tube indicates a maximum diameter of a device (medical instrument such as catheter 70) that can be inserted into the inner lumen of the sheath tube. In addition, as shown in FIGS. 5(A) and 5(C), the inner diameter dimension $\phi 4$ can be increased ($\phi 4 > \phi 1$) at the same outer diameter dimension $\phi 2$ by reducing the wall thickness (t=T3, T1>T3) of the sheath tube 102. Therefore, the inner diameter dimension $\phi 4$ allows insertion of a device possessing an even larger outer diameter. On the other hand, as shown in FIGS. 5(A) and 5(D), the size of the inner diameter dimension $\phi 5$ is also reduced ($\phi 1 > \phi 5$) even when the size of the outer diameter dimension $\phi 3$ is reduced by one Fr size ($\phi 2 > \phi 3$) with the wall thickness (t=T1) of the sheath tube 103 being maintained. As a result, only a device possessing a relatively small outer diameter dimension can be inserted.

The range of applications is extended as follows by reducing the wall thickness of the sheath tube 21. Because the outer diameter of the introducer sheath (7 Fr size introducer sheath) into which a medical device having 7 Fr (7 Fr outer diameter) is inserted was larger than the blood vessel diameter (approximately 2.9±0.6 mm) of radial artery, it is impossible to perform TRI procedure using the device such as the catheter 70 having 7 Fr. Herein, the outer diameter dimension of the introducer sheath can be reduced in size by one Fr (6 Fr size) at the same inner diameter dimension by reducing the wall thickness of the introducer sheath 20. In this manner, it is possible to perform TRI procedure using the device having 7 Fr. The device (medical device) with an outer diameter of 7 Fr can be inserted into the introducer sheath with an outer diameter of 6 Fr size. In the present specification, such device size-sheath size combination is referred to as "7 in 6". That is, the introducer sheath expressed as "7 in 6" means the inner diameter of the introducer sheath is sized to receive a device (medical device) having an outer diameter of 7 Fr, and the outer diameter of the introducer sheath is equivalent to an outer diameter of a known introducer sheath corresponding to 6 Fr size. Thinning the wall thickness of a known 7 Fr introducer sheath makes possible the above-described "7 in 6" introducer sheath. A medical device possessing 7 Fr outer diameter can be inserted into an introducer sheath expressed as "7 in 6".

The device size-sheath size combination is not limited to the "7 in 6" and can be applied to all sizes. For example, all outer diameter sizes can be reduced by one Fr size as "11 in 10", "10 in 9", "9 in 8", "8 in 7", "7 in 6", "6 in 5", "5 in 4", "4 in 3", and "3 in 2".

Furthermore, as the sheath outer diameter dimension is reduced by one Fr size, an insertion mark (incision) of the human body becomes smaller and the hemostasis time is shortened. Accordingly, the hospital stay time is shortened and a physical burden on a patient and an economic burden on the hospital become lighter.

As described above, the size of the outer diameter dimension can be reduced by one Fr size at the same inner diameter dimension by reducing the wall thickness of the sheath tube 21. However, in regards to the introducer 10 provided with the sheath tube 21 in which the wall thickness is reduced, in a case where the color code which is the same as that of the previous sheath tube is used, it is impossible to easily recognize the difference with an introducer 10 provided with the previous sheath tube in which the wall thickness is not reduced. In addition, in regards to the sheath tube 21 in which the wall thickness is reduced, it is impossible to recognize the relationship between the inner diameter and the outer diameter.

The introducer 10 of the present embodiment which addresses the above-described problem caused when the wall thickness of the sheath tube 21 is reduced will be described in detail.

As described above, the introducer 10 of the present embodiment has the introducer sheath 20 and the dilator 30.

The introducer sheath 20 includes the elongated hollow sheath tube 21 and the sheath hub 22 which is provided at the proximal side of the sheath tube 21 and provided with the insertion port 25a through which the dilator 30 is inserted. The dilator 30 includes a dilator tube 31 which is inserted into the sheath tube 21 and a dilator hub 32 which is provided at the proximal side of the dilator tube 31. The introducer 10 further includes a first information piece 51 which is shown on at least one of the introducer sheath 20 and the dilator 30 and has the inner diameter dimension of the sheath tube 21 as an index, and a second information piece 52 which is shown on at least one of the introducer sheath 20 and the dilator 30 and has the outer diameter dimension of the sheath tube 21 as an index.

In the present embodiment, the first information piece 51 is configured of a color and the second information piece 52 is also configured of a color.

The portions of the introducer 10 to show the first information piece 51 and the second information piece 52 can be appropriately modified. In the present embodiment, the first information piece 51 or the second information piece 52 is shown on members (sheath tube 21 and sheath hub 22) included in the introducer sheath 20 and the first information piece 51 or the second information piece 52 is shown on members (dilator tube 31 and a dilator hub 32) included in the dilator 30. The possible combinations of information and location are listed in the following Table 1.

TABLE 1

| Combination | First information piece 51 (using inner diameter dimension of sheath tube 21 as index) | Second information piece 52 (using outer diameter dimension of sheath tube 21 as index) |
| --- | --- | --- |
| 1 | introducer sheath 20 | dilator 30 |
| 2 | dilator 30 | introducer sheath 20 |
| 3 | dilator 30 | dilator 30 |
| 4 | Introducer sheath 20 | Introducer sheath 20 |

As described above, the Fr size of the sheath tube 21 shows the maximum diameter of the device that can be inserted into the lumen of the sheath tube 21. For example, there is a case where the first information piece 51 is a Fr size of the sheath tube 21 having an inner diameter dimension of the sheath tube 21 as an index and the second information piece 52 is a Fr size of the sheath tube 21 having an outer diameter dimension of the sheath tube 21 as an index. In this case, the first information piece 51 and the second information piece 52 are the same as each other in a case of the previous sheath tube of which the wall thickness is not reduced. On the other hand, in a case of the sheath tube 21 in which the wall thickness is reduced, it is possible to reduce the size of the outer diameter dimension by, for example, reducing one Fr size at the same inner diameter dimension, and therefore, the first information piece 51 and the second information piece 52 are different from each other. In other words, when the first information piece 51 and the second information piece 52 are the same as each other, a user can easily identify that the used introducer is the introducer 10 provided with the previous sheath tube in which the wall thickness is not reduced. On the other hand, when the first information piece 51 and the second information piece 52 are different from each other, a user can easily identify that the used introducer is the introducer 10 provided with the sheath tube 21 in which the wall thickness is reduced.

In this manner, since the introducer 10 is provided with the first information piece 51 having the inner diameter dimension of the sheath tube 21 as an index and the second information piece 52 having the outer diameter dimension of the sheath tube 21 as an index, it is possible to easily recognize the difference between the introducer 10 provided with the sheath tube 21 of which the wall thickness is reduced and the introducer 10 provided with the previous sheath tube in which the wall thickness is not reduced.

Furthermore, since the introducer 10 is provided with the first information piece 51 having the inner diameter dimension of the sheath tube 21 as an index and the second information piece 52 having the outer diameter dimension of the sheath tube 21 as an index, the relationship between the inner diameter and the outer diameter becomes clear with respect to the sheath tube 21 in which the wall thickness is reduced.

In this manner, a user such as a doctor or a nurse can recognize whether or not the sheath tube is the sheath tube 21 in which the wall thickness is reduced and can recognize the relationship between the inner diameter and the outer diameter with respect to the sheath tube 21 in which the wall thickness is reduced while preparing or using the introducer 10. Accordingly, it is possible to smoothly and promptly proceed with the preparation work of a device to be inserted next and to prevent misidentification of the device size.

It is possible to select portions of the introducer 10 to show the first information piece 51 and the second information piece 52. Moreover, individual members (sheath tube 21 and sheath hub 22) which are included in the introducer sheath 20 can be set to show the first information piece 51 or the second information piece 52 and individual members (dilator tube 31 and a dilator hub 32) which are included in the dilator 30 can be set to show the first information piece 51 or the second information piece 52.

Here, it is preferable that the first information piece 51 be shown (located) at a position closer to the proximal portion of the dilator 30 than the second information piece 52.

When a user inserts the dilator tube 31 into the sheath tube 21, the user grips and presses the dilator hub 32 closer to the proximal portion of the dilator 30. Accordingly, the inner diameter of the sheath tube 21 is shown at a position closer to the proximal portion of the dilator 30. Therefore, it is easy to recognize the maximum size of a device that can be inserted into the insertion port 25a.

From this perspective, as shown in the second combination in Table 1, it is preferable that the first information piece 51 be shown on the dilator 30 and the second information piece 52 be shown on the introducer sheath 20.

It is possible to employ a mode of showing the first information piece 51 or the second information piece 52 on individual members included in the sheath hub 22 as well as showing the first information piece 51 or the second information piece 52 on the entire sheath hub 22. The mode will be described below.

The sheath hub 22 of the present embodiment includes the sheath support body 23 which is provided at the proximal side of the sheath tube 21, the housing 24 which is provided at the proximal side of the sheath support body 23, the cap 25 which is attached to the housing 24 and at which the insertion port 25a is formed, and a tab portion 26 in which a hole portion 26a is formed in order to fix the introducer sheath 20. The dilator includes the dilator tube 31 and the dilator hub 32. Moreover, the first information piece 51 and the second information piece 52 can be shown on at least one of the sheath support body 23, housing 24, cap 25, and tab portion 26 in the sheath hub 22. In addition, the first information piece 51 and the second information piece 52 can be shown on at least one of the dilator tube 31 and the dilator hub 32. The combinations when showing the first information piece 51 on the dilator 30 and the second information piece 52 on the introducer sheath 20 are set forth in the following Table 2.

TABLE 2

| Combination | First information piece 51 (inner diameter dimension of sheath tube 21) | Second information piece 52 (outer diameter dimension of sheath tube 21) |
| --- | --- | --- |
| 1 | Dilator tube 31 | Sheath support body 23 |
| 2 | Dilator tube 31 | Housing 24 |
| 3 | Dilator tube 31 | Cap 25 |
| 4 | Dilator tube 31 | Tab portion 26 |
| 5 | Dilator hub 32 | Sheath support body 23 |
| 6 | Dilator hub 32 | Housing 24 |
| 7 | Dilator hub 32 | Cap 25 |
| 8 | Dilator hub 32 | Tab portion 26 |

As described above, in order to facilitate easy recognition of the maximum size of a device that can be inserted into the insertion port 25a of the sheath hub 22, it is preferable that the first information piece 51 be shown at a position closer to the proximal portion of the dilator 30 than the second information piece 52. From this perspective, as shown in the fifth to the eighth combinations in Table 2, the first information piece 51 may be shown on the dilator hub 32 and the second information piece 52 may be shown on the members constituting the sheath hub 22. In this case, the second information piece 52 may be shown on an integrated part in which two members, the sheath support body 23 and the tab portion 26, are integrally formed. In addition, the second information piece 52 may be shown on an integrated part in which three members, the sheath support body 23, the housing 24, and the tab portion 26, are integrally formed. In addition, the first information piece 51 may also be shown on an integrated part in which two members, the dilator tube 31 and the dilator hub 32, are integrally formed.

The sheath tube 21 which is applied to the introducer 10 will be described with reference to FIGS. 6(A) to 6(C). The sheath tube 21 to be applied includes a combination of three kinds of sheath tubes such as a first sheath tube 61 to a third sheath tube 63 to be described below.

As shown in FIG. 6(A), in the first sheath tube 61, the wall thickness is T1, the outer diameter dimension is D1, and the inner diameter dimension is D1i. There is an example of the previous sheath tube in which the wall thickness is not reduced and has a 5 Fr size.

As shown in FIG. 6(B), in the second sheath tube 62, the wall thickness is T1 which is the same as the wall thickness in the first sheath tube 61, the outer diameter dimension is D2(D1<D2) which is a size larger than the outer diameter dimension of the first sheath tube 61, and the inner diameter dimension is D2i. For example, the sheath tube is the previous sheath tube in which the wall thickness is not reduced and has a 6 Fr size.

As shown in FIG. 6(C), in the third sheath tube 63, the wall thickness is T2 (T2<T1) which is thinner than the wall thicknesses of the first and the second sheath tubes 61 and 62, the outer diameter dimension is D3o (D1<D3o<D2o) which is larger than the outer diameter dimension D1o of the first sheath tube 61 and smaller than the outer diameter dimension D2o of the second sheath tube 62, and the inner diameter dimension is D3i (D1i<D3i≤D2i) which is larger than the inner diameter dimension D1i of the first sheath tube 61 and not larger than the inner diameter dimension D2i of the second sheath tube 62. The third sheath tube 63 is the sheath tube 21 in which the wall thickness is reduced. The outer diameter dimension of the third sheath tube 63 is the same as the outer diameter dimension of the previous sheath tube 21 with a 5 Fr size and the inner diameter dimension of the third sheath tube 63 is the same as the inner diameter dimension of the previous sheath tube 21 with a 6 Fr size, and therefore, it is possible to insert a device having a size 6 Fr therein. According to the way of expression in the present specification, the structure is referred to as a sheath tube 21 with a 6- in 5-Fr size. Moreover, the first information piece 51 (that is, the information of the inner diameter dimension) which is shown when applied to the third sheath tube 63 (6- in 5-Fr) is the same as the first information piece 51 which is shown when applied to the second sheath tube 62 (6 Fr) and the second information piece 52 (that is, the information of the outer diameter dimension) which is shown when applied to the third sheath tube 63 (6- in 5-Fr) is the same as the second information piece 52 which is shown when applied to the first sheath tube 61 (5 Fr).

Next, another embodiment of the sheath tube 21 which is applied to the introducer 10 will be described with reference to FIGS. 7(A) to 7(C). The sheath tube 21 to be applied includes a combination of three kinds of sheath tubes such as a first sheath tube 71 to a third sheath tube 73 to be described below.

As shown in FIG. 7(A), in the first sheath tube 71, the wall thickness is t1, the outer diameter dimension is d1o, and the inner diameter dimension is d1i. There is an example of the previous sheath tube in which the wall thickness is not reduced and has a 5 Fr size.

As shown in FIG. 7(B), in the second sheath tube 72, the wall thickness is t1 which is the same as the wall thickness in the first sheath tube 71, the outer diameter dimension is d2o (d1o<d2o) which is set to be a size larger than the outer diameter dimension of the first sheath tube 71, and the inner diameter dimension is d2i. For example, the sheath tube is the previous sheath tube in which the wall thickness is not reduced and has a 6 Fr size.

As shown in FIG. 7(C), in the third sheath tube 73, the wall thickness is t2 (t2 <t1) which is thinner than the wall thicknesses of the first and the second sheath tubes 71 and 72, the outer diameter dimension is d3o (d3o<d1o<d2o) which is smaller than the outer diameter dimension d1o of the first sheath tube 71 and smaller than the outer diameter dimension d2o of the second sheath tube 72, and the inner diameter dimension is d3i (d1i<d3i≤d2i) which is larger than the inner diameter dimension d1i of the first sheath tube 71 and not larger than the inner diameter dimension d2i of the second sheath tube 72. The third sheath tube 73 is the sheath tube 21 of which the wall thickness is reduced. The outer diameter dimension of the third sheath tube 73 is smaller than that of the previous sheath tube 21 with a 5 Fr size and the inner diameter dimension of the third sheath tube 73 is smaller than or equal to that of the previous sheath tube 21 with a 6 Fr size, and therefore, it is possible to insert a device having a 6 Fr therein. According to the way of expression in the present specification, the structure is referred to as a sheath tube 21 with a 6-in 5-Fr size. Moreover, the first information piece 51 (that is, the information of the inner diameter dimension) which is shown when applied to the third sheath tube 73 (6- in 5-Fr) is the same as the first information piece 51 which is shown when applied to the second sheath tube 72 (6 Fr) and the second information piece 52 (that is, the information of the outer diameter dimension) which is shown when applied to the third sheath tube 73 (6- in 5-Fr) is the same as the second information piece 52 which is shown when applied to the first sheath tube 71 (5 Fr).

Specific examples of the color codes are set forth in the following Tables 3 and 4. An example in which the first information piece 51 is shown on the dilator hub 32 and the second information piece 52 is shown on the sheath support body 23 is shown in Table 3. An example in which the first information piece 51 is shown on the dilator hub 32 and the second information piece 52 is shown on the housing 24 is shown in Table 4. Note that colors which are different from the exemplified color codes, that is, colors which are not shown by the French sizes of the color codes may be shown.

support body 23. In addition, it is unnecessary to use the same colors and colors which are not shown by the Fr size of the sheath tube 21 may be used.

As is exemplified in Tables 3 and 4, in a case where the first information piece 51 is a Fr size of the sheath tube 21 having an inner diameter dimension of the sheath tube 21 as an index and the second information piece 52 is a Fr size of the sheath tube 21 having an outer diameter dimension of the sheath tube 21 as an index, the first information piece 51 and the second information piece 52 are the same as each other in a case of the previous sheath tube in which the wall thickness is not reduced. On the other hand, in a case of the sheath tube 21 in which the wall thickness is reduced, it is possible to reduce the size of the outer diameter dimension by, for example, one Fr size at the same inner diameter dimension, and therefore, the first information piece 51 and the second information piece 52 are different from each other. In other words, when the first information piece 51 and the second information piece 52 are the same as each other (when the same color is used for the sheath support body 23 and the dilator hub 32 in the present embodiment), a user can easily identify that the used introducer is the introducer 10 provided with the previous sheath tube in which the wall thickness is not reduced. Meanwhile, when the first information piece 51 and the second information piece 52 are different from each other (when different colors are used for the sheath support body 23 and the dilator hub 32 in the present embodiment), a user can easily identify that the used introducer is the introducer 10 provided with the sheath tube 21 whose wall thickness is reduced.

TABLE 3

| Size | Outer diameter | Inner diameter | Second information piece 52 on sheath support body 23 (visualization of outer diameter) | First information piece 51 on dilator hub 32 (visualization of inner diameter) | Combination of colors |
| --- | --- | --- | --- | --- | --- |
| 7 in 6 | 6 Fr | 7 Fr | 6 Fr color (green) | 7 Fr color (orange) | Different colors |
| 6 | 6 Fr | 6 Fr | 6 Fr color (green) | 6 Fr color (green) | Same colors |
| 6 in 5 | 5 Fr | 6 Fr | 5 Fr color (grey) | 6 Fr color (green) | Different colors |
| 5 | 5 Fr | 5 Fr | 5 Fr color (grey) | 5 Fr color (grey) | Same colors |
| 5 in 4 | 4 Fr | 5 Fr | 4 Fr color (red) | 5 Fr color (grey) | Different colors |
| 4 | 4 Fr | 4 Fr | 4 Fr color (red) | 4 Fr color (red) | Same colors |
| 4 in 3 | 3 Fr | 4 Fr | 3 Fr color (purple) | 4 Fr color (red) | Different colors |

In the combination shown in Table 3, the color code which is the same as the sheath support body 23 may be shown on the housing 24. In addition, it is unnecessary to use the same colors and colors which are not shown by the Fr size of the sheath tube 21 may be used.

In this manner, since the introducer 10 is provided with the first information piece 51 having the inner diameter dimension of the sheath tube 21 as an index and the second information piece 52 having the outer diameter dimension of the sheath tube 21 as an index, it is possible to easily

TABLE 4

| Size | Outer diameter | Inner diameter | Second information piece 52 on housing 24 (visualization of outer diameter) | First information piece 51 on dilator hub 32 (visualization of inner diameter) | Combination of colors |
| --- | --- | --- | --- | --- | --- |
| 7 in 6 | 6 Fr | 7 Fr | 7 Fr color (orange) | 6 Fr color (green) | Different colors |
| 6 | 6 Fr | 6 Fr | 6 Fr color (green) | 6 Fr color (green) | Same colors |
| 6 in 5 | 5 Fr | 6 Fr | 6 Fr color (green) | 5 Fr color (grey) | Different colors |
| 5 | 5 Fr | 5 Fr | 5 Fr color (grey) | 5 Fr color (grey) | Same colors |
| 5 in 4 | 4 Fr | 5 Fr | 5 Fr color (grey) | 4 Fr color (red) | Different colors |
| 4 | 4 Fr | 4 Fr | 4 Fr color (red) | 4 Fr color (red) | Same colors |
| 4 in 3 | 3 Fr | 4 Fr | 4 Fr color (red) | 3 Fr color (purple) | Different colors |

In the combination shown in Table 4, the color code which is the same as the housing 24 may be shown on the sheath recognize the difference between the introducer 10 provided with the sheath tube 21 whose wall thickness is reduced and the introducer 10 provided with the previous sheath tube whose wall thickness is not reduced.

Furthermore, since the introducer 10 is provided with the first information piece 51 having the inner diameter dimension of the sheath tube 21 as an index and the second information piece 52 having the outer diameter dimension of the sheath tube 21 as an index, the relationship between the inner diameter and the outer diameter becomes clear with respect to the sheath tube 21 whose wall thickness is reduced.

In this manner, a user such as a doctor or a nurse can recognize whether or not the sheath tube is the sheath tube 21 in which the wall thickness is reduced and can recognize the relationship between the inner diameter and the outer diameter with respect to the sheath tube 21 in which the wall thickness is reduced while preparing or using the introducer 10. Accordingly, it is possible to smoothly and promptly proceed with the preparation work of a device to be inserted next and to prevent misidentification of the device size.

The third sheath tube 63 shown in FIG. 6(C) is the sheath tube 21 in which the wall thickness is reduced compared to the first and the second sheath tubes 61 and 62. The outer diameter dimension D3o of the third sheath tube 63 is the same as the outer diameter dimension of the first sheath tube 61 and the inner diameter dimension d3i is the same as the inner diameter dimension of the second sheath tube 62. Therefore, it is possible to insert a device having a size larger while reducing the size of the outer diameter. The above-described effect can be exhibited in regards to the introducer 10 provided with such a sheath tube 21.

In addition, the third sheath tube 73 shown in FIG. 7(C) is the sheath tube 21 in which the wall thickness is reduced compared to the wall thicknesses of the first and the second sheath tubes 71 and 72, and the outer diameter dimension d3o of the third sheath tube 73 is smaller than the outer diameter dimension of the first and the second sheath tubes 71 and 72. Therefore, it is possible to insert a device by reducing the size of the outer diameter. In addition, when the inner diameter dimension d3i is a size between the inner diameter dimensions d1i and the d2i of the first and the second sheath tubes 71 and 72, a device having a size larger can be inserted. The above-described effect can be exhibited in regards to the introducer 10 provided with such a sheath tube 21.

The embodiment in which the first information piece 51 is configured of a color and the second information piece 52 is also configured of a color was described, but the disclosure here is not limited to such an example. The first information piece 51 may be at least one of a color and a figure and the second information piece 52 may be at least one of a color and a figure. Possible combinations which can be employed are set forth in the following Table 5.

TABLE 5

| Combination | First information piece 51 (inner diameter dimension of sheath tube 21) | Second information piece 52 (outer diameter dimension of sheath tube 21) |
| --- | --- | --- |
| 1 | Color | Color |
| 2 | Color | Figure |
| 3 | Figure | Color |
| 4 | Figure | Figure |
| 5 | Color + figure | Color |
| 6 | Color + figure | Figure |
| 7 | Color | Color + figure |

TABLE 5-continued

| Combination | First information piece 51 (inner diameter dimension of sheath tube 21) | Second information piece 52 (outer diameter dimension of sheath tube 21) |
| --- | --- | --- |
| 8 | Figure | Color + figure |
| 9 | Color + figure | Color + figure |

In this manner, it is possible to simply show the first and the second information pieces 51 and 52 using a color and a figure.

The first and the second information pieces 51 and 52 are not limited to the case of being a color or a figure. A character may be used in addition to a color or a figure. In addition, it is possible that the first and the second information pieces 51 and 52 are configured of a shape. For example, it is possible to show the first and the second information pieces 51 and 52 by providing a plurality of kinds of projection shapes on the sheath hub 22 or the like in the required number. It is predetermined that a projection shape in which the cross section has a square shape indicates "5" and a projection shape in which the cross section has a semi-circular shape indicates "1". Then, the sheath hub 22 may be provided with "6" for the first information piece 51 or the second information piece 52 in a case where a projection shape in which the cross section has a square shape is provided and a projection shape in which the cross section has a semi-circular shape is provided. In a case of showing the information using the shape, it is possible to recognize the information through tactile sense in addition to visual sense.

The detailed description above describes embodiments of an introducer representing examples of the introducer disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An introducer comprising:
an introducer sheath including an elongated hollow sheath tube and a sheath hub which is provided at a proximal side of the sheath tube and provided with an insertion port;
a dilator having a dilator tube which is configured to be inserted into the sheath tube and a dilator hub which is provided at a proximal side of the dilator tube, the insertion port being configured to permit the dilator to be inserted into the insertion port; and
a first information piece on at least one of the introducer sheath and the dilator which identifies the inner diameter dimension of the sheath tube as being the inner diameter dimension associated with a first Fr size; and
a second information piece on said at least one of the introducer sheath and the dilator which identifies the outer diameter dimension of the sheath tube as a second Fr size;
wherein the first information piece identifies a maximum diameter of medical device that can be inserted into a lumen of the sheath tube;

wherein the sheath tube has a reduced wall thickness; and wherein the second information piece indicates the outer diameter dimension of the sheath tube as one Fr size smaller than the first Fr size indicated by the first information piece.

2. The introducer according to claim 1, wherein the first information piece or the second information piece shown on the dilator is shown on at least one of the dilator tube and the dilator hub, and wherein the first information piece or the second information piece shown on the introducer sheath is shown on at least one of the sheath tube and the sheath hub.

3. The introducer according to claim 1, wherein the first information piece is shown at a position closer to a proximal portion of the dilator than the second information piece.

4. The introducer according to claim 1, wherein the sheath hub includes a sheath support body which is provided at the proximal side of the sheath tube; a housing which is provided at a proximal side of the sheath support body; a cap which is attached to the housing and at which the insertion port is formed; and a tab portion in which a through hole is formed in order to fix the introducer sheath, wherein the first information piece is on at least one of the sheath support body, the housing, the cap, and the tab portion in the sheath hub, and wherein the second information piece is on at least one of the sheath support body, the housing, the cap, and the tab portion in the sheath hub.

5. The introducer according to claim 1, wherein the first information piece is at least one of a color or a figure, and wherein the second information piece is at least one of a color or a figure.

6. The introducer according to claim 1, wherein the first information piece is on the introducer sheath, and wherein the second information piece is on the dilator.

7. The introducer according to claim 1, wherein the sheath hub includes a sheath support body at the proximal side of the sheath tube; a housing at a proximal side of the sheath support body; a cap attached to the housing and at which the insertion port is formed; and a tab portion in which a hole is formed to positionally fix the introducer sheath, wherein the first information piece is on at least one of the sheath support body, the housing, the cap, and the tab portion in the sheath hub.

8. The introducer according to claim 7, wherein the second information piece is on at least one of the dilator tube and the dilator hub.

9. The introducer according to claim 1, wherein the sheath hub includes a sheath support body at a proximal side of the sheath tube; a housing at a proximal side of the sheath support body; a cap attached to the housing and at which the insertion port is formed; and a tab portion provided with a through hole to positionally fix the introducer sheath, and wherein the second information piece is on at least one of the sheath support body, the housing, the cap, and the tab portion in the sheath hub.

10. The introducer according to claim 9, wherein the first information piece is on at least one of the dilator tube and the dilator hub.

11. An introducer comprising:

an introducer sheath including an elongated hollow sheath tube and a sheath hub, the elongated hollow sheath tube possessing a proximal end and the sheath hub being connected to the proximal end of the sheath tube, with a portion of the elongated hollow sheath tube and a portion of the sheath hub axially overlapping each other, the sheath hub including an insertion port configured to permit insertion of a dilator into the insertion port, the sheath tube possessing an outer diameter and an inner diameter; and a dilator having a dilator tube which is configured to be inserted into the sheath tube and a dilator hub which is provided at a proximal side of the dilator tube; and a first information piece on the introducer sheath or the dilator which identifies an inner diameter dimension of the introducer sheath or the dilator as being the inner diameter dimension associated with a first Fr size, and a second information piece on the introducer sheath or the dilator which indicates the outer diameter dimension of the introducer sheath or dilator as one Fr size smaller than the first Fr size indicated by the first information piece, the first and second information pieces being different from one another and identifying the sheath tube of the introducer sheath as possessing a reduced wall thickness relative to another sheath tube of another introducer sheath that possesses either an inner diameter or an outer diameter the same as the inner diameter or the outer diameter, respectively, of the sheath tube of the introducer.

12. The introducer according to claim 11, wherein the first information piece is on the introducer sheath, and wherein the second information piece is on the dilator.

13. The introducer according to claim 12, wherein the sheath hub includes a sheath support body at a proximal side of the sheath tube; a housing at a proximal side of the sheath support body; a cap attached to the housing and at which the insertion port is formed; and a tab portion provided with a through hole to positionally fix the introducer sheath, wherein the first information piece is on at least one of the sheath support body, the housing, the cap, and the tab portion in the sheath hub.

14. The introducer according to claim 13, wherein the second information piece is on at least one of the dilator tube and the dilator hub.

15. The introducer according to claim 11, wherein the sheath hub includes a sheath support body at a proximal side of the sheath tube; a housing at a proximal side of the sheath support body; a cap attached to the housing and at which the insertion port is formed; and a tab portion provided with a through hole to positionally fix the introducer sheath, and wherein the second information piece is on at least one of the sheath support body, the housing, the cap, and the tab portion in the sheath hub.

16. The introducer according to claim 15, wherein the first information piece is on at least one of the dilator tube and the dilator hub.

17. The introducer according to claim 11, wherein the first information piece includes a color and the second information piece includes a color.

18. The introducer according to claim 11, wherein the first information piece is at least one of a color and a figure, and the second information piece is at least one of a color and a figure.

19. The introducer according to claim 11, wherein the first information piece and the second information piece are both provided on the introducer sheath or on the dilator.

* * * * *